United States Patent
Anders et al.

(10) Patent No.: US 11,940,642 B2
(45) Date of Patent: Mar. 26, 2024

(54) ILLUMINATION DEVICE FOR FLUORESCENCE IMAGE GUIDED SURGERY AND SURGICAL INSTRUMENT

(71) Applicant: OLYMPUS Winter & Ibe GmbH, Hamburg (DE)

(72) Inventors: Konrad Anders, Hamburg (DE); Matthias Dissel, Hamburg (DE); Jens Klinder, Hamburg (DE); Sven Pabst, Giekau (DE); Timo Pfander, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 18/225,773

(22) Filed: Jul. 25, 2023

(65) Prior Publication Data
US 2024/0053526 A1   Feb. 15, 2024

Related U.S. Application Data

(60) Provisional application No. 63/397,480, filed on Aug. 12, 2022.

(51) Int. Cl.
*F21V 8/00*     (2006.01)
*A61B 5/00*     (2006.01)
*A61B 90/30*    (2016.01)

(52) U.S. Cl.
CPC .......... *G02B 6/0008* (2013.01); *A61B 5/0071* (2013.01); *A61B 90/30* (2016.02); *G02B 6/0006* (2013.01); *A61B 2090/306* (2016.02); *A61B 2090/309* (2016.02)

(58) Field of Classification Search
CPC ..... A61B 5/0059; A61B 5/0071; A61B 90/30; A61B 2090/304–309; G02B 6/003–001
See application file for complete search history.

(56) References Cited

U.S. PATENT DOCUMENTS

| | | |
|---|---|---|
| 4,403,273 A | 9/1983 | Nishioka |
| 6,547,721 B1 | 4/2003 | Higuma |
| 2013/0156389 A1 | 6/2013 | Shinji et al. |

FOREIGN PATENT DOCUMENTS

| | | |
|---|---|---|
| DE | 32 02 080 A1 | 10/1982 |
| DE | 699 23 388 T2 | 12/2005 |
| DE | 10 2008 052 829 A1 | 4/2010 |
| DE | 10 2009 040 093 A1 | 4/2011 |
| DE | 10 2015 102 595 A1 | 8/2016 |
| DE | 10 2016 216 443 A1 | 3/2018 |

*Primary Examiner* — Jason M Han
(74) *Attorney, Agent, or Firm* — Scully, Scott, Murphy & Presser, P.C.

(57) ABSTRACT

An illumination device for fluorescence image guided surgery and a surgical instrument. The illumination device includes a glass rod, a mixing rod and a plurality of optical fibers surrounding a circumferential surface of the glass rod. A first mixing rod end face of the mixing rod abuts a second rod end face of the glass rod and end faces of the optical fibers, so that white light and excitation light are guided and homogenized in the mixing rod.

23 Claims, 3 Drawing Sheets

ILLUMINATION DEVICE FOR FLUORESCENCE IMAGE GUIDED SURGERY AND SURGICAL INSTRUMENT

CROSS-REFERENCE TO RELATED APPLICATION

The present application is based upon and claims the benefit of priority from U.S. Provisional Application No. 63/397,480, filed on Aug. 12, 2022, the entire contents of which is incorporated herein by reference.

BACKGROUND

Field

The present disclosure relates to an illumination device for fluorescence image guided surgery. The present disclosure further relates to a surgical instrument comprising such an illumination device.

Prior Art

Fluorescence image guided surgery is a technique utilized to highlight certain areas or masses of interest during surgery to aid in navigation. In this technique, fluorescent dyes and/or fluorescent proteins are used to mark certain molecules in the surgical area. When radiated with excitation light of appropriate wavelength, the so marked molecules will emit fluorescent light. The fluorescent light can be detected either directly by the surgeon or by a camera system, if the wavelength of the fluorescent light is outside the visible spectrum.

Fluorescence can be used both in open surgeries and minimal invasive surgeries. In both of these types, the surgeon requires a source of white light in addition to the excitation light. The white light is necessary to illuminate the surgical area, so that he can perceive the area surrounding the marked molecules.

Both the excitation light and the white light are often coupled into the same light guide, for example in the form of an optical fiber cable. This optical fiber cable, called an external optical fiber cable, is then utilized to guide the light to the surgical area and illuminate it with both the white light and the excitation light.

To couple the light into the external optical fiber cable, the white light and the excitation light are often guided in separate, internal optical fibers to the interface with the external optical fiber cable. However, at this interface, there is the risk of a loss of light intensity, caused by the end faces of the individual fibers not being completely aligned. In addition, the internal optical fibers used to guide the white light may be damaged when exposed to high power intensities from bright white light sources. Also, the output at the end of the external optical fiber cable is usually not homogeneous, as the intensity of the white light and the excitation light will have minima and maxima at the end face. This may result in some very bright light points. When using laser light as excitation light, this requires a higher laser class for the illumination assembly than would otherwise be necessary.

SUMMARY

It is an object to provide a bright and homogeneous illumination for fluorescence image guided surgery.

Such object can be solved by an illumination device for fluorescence image guided surgery, comprising a white light guiding portion, an excitation light guiding portion and a mixed light guiding portion, wherein the white light guiding portion comprises a glass rod extending in a longitudinal direction from a first rod end, configured to receive white light, to a second rod end, configured to emit the white light, the glass rod comprising a first rod end face at the first rod end, a second rod end face at the second rod end and a circumferential surface extending between the first rod end face and the second rod end face, wherein the excitation light guiding portion comprises a plurality of optical fibers, each extending from a first fiber end, configured to receive excitation light, to a second fiber end, configured to emit the excitation light, wherein the second fiber ends of the plurality of optical fibers surround the circumferential surface of the glass rod at the second rod end, wherein the mixed light guiding portion comprises an optical mixing rod extending in the longitudinal direction from a first mixing rod end, configured to receive the white light and the excitation light, to a second mixing rod end, configured to emit mixed light, the mixing rod comprising a first mixing rod end face at the first mixing rod end, a second mixing rod end face at the second mixing rod end and a circumferential surface extending between the first mixing rod end face and the second mixing rod end face, wherein the glass rod is arranged to couple the white light guided in the glass rod into the mixing rod via the second rod end face of the glass rod and the first mixing rod end face of the mixing rod, wherein each of the optical fibers is arranged to couple the excitation light guided in the optical fibers into the mixing rod via end faces at the second fiber ends of the optical fibers and the first mixing rod end face of the mixing rod.

The illumination device can provide a bright and homogeneous light output. The illumination device may be used for minimal invasive surgery, for example with an endoscope. In addition, the illumination device may be used for open surgeries.

The white light can be coupled into the glass rod instead of an optical fiber, which can withstand higher intensities than an optical fiber without getting damaged. Thus, white light with higher intensity can be used for the surgery. In addition, the glass rod homogenizes the white light guided within, so that the intensity of the white light is distributed equally over the second rod end face of the glass rod.

The excitation light can be guided in the optical fibers. The second fiber ends of the optical fibers, where the excitation light is emitted, can be arranged to surround the circumferential surface of the glass rod at the second rod end where the white light is emitted. In other words, the excitation light can be emitted in a ring-like fashion around the second rod end face, where the white light is emitted.

Both the white light and the excitation light can be coupled into the first mixing rod end face of the mixing rod. Afterwards, they can both be guided within the mixing rod, where the intensity of both the white light and the excitation light is homogenized. At the second mixing rod end face, both the white light and the excitation light exit the mixing rod in a homogenized state and are thereafter called mixed light. As the intensity of the white light and the intensity of the excitation light are spread equally over the second mixing rod end face, the resulting mixed light is homogeneous and does not comprise bright light points.

Both the glass rod and the mixing rod can extend along the longitudinal direction. The second fiber ends can be arranged to emit the excitation light essentially in the longitudinal direction. In the context of the present description, the longitudinal direction is the direction in which the mixed light is emitted.

The glass rod can be made from a glass or comprises a glass. The optical mixture rod can be transparent and can be made from a glass and/or a transparent plastic material, for example polymethylmethacrylate, polycarbonate, cyclic olefin polymer or cyclic olefin copolymer.

The excitation light can be visible light and/or infrared light and/or UV light and/or light of other suitable wavelengths for fluorescence image guided surgery.

The glass rod and/or the mixture rod can have a cylindrical shape, wherein the second fiber ends of the plurality of optical fibers can be arranged to completely surround the circumferential surface at the second rod end of the glass rod. The cylindrical shape can guide the light from the first end faces to the second end faces and simultaneously homogenizing the intensity of the guided light. The circumferential surface of the glass rod and/or the mixture rod can be a cylindrical surface. According to an embodiment, the glass rod and/or the mixture rod can have a hexagonal cross section. Hexagonal rods can also achieve good light mixing results. The glass rod and/or the mixture rod can have a rod shape other than cylindrical or hexagonal, as well.

According to an embodiment, the glass rod and/or the mixture rod can comprise a rod core and a cladding, wherein the cladding surrounds the rod core along a circumference of the rod core and has a lower refractive index than the rod core. The rod core guides the light inside the rod. The cladding, which surrounds the rod core, reflects the light back into the rod core, when it hits the interface between rod core and cladding. In principle, total reflection is also possible without the cladding, as light can be totally reflected at the surface extending along the circumference of the rod core and the ambient air surrounding it. However, the cladding simplifies the fixture of the glass rod and/or mixture rod in a sleeve, because the cladding can be fixed, e.g. glued, in the sleeve without impairing the total reflection on the interface between the rod core and the cladding.

A length of the mixture rod can be at least five times greater than a diameter of the mixture rod. By providing the mixture rod with a length five times greater than its diameter, the white light and the excitation light guided inside the mixture rod can be evenly homogenized. The length of the glass rod can be at least five times greater than a diameter of the glass rod.

According to an embodiment, the second fiber ends can be arranged to form an annular, flat emitter around the second rod end of the glass rod. By arranging the fiber ends to form an annular, flat emitter, the excitation light can be emitted in a ring-like fashion. The second fiber ends can be distributed equally around the annular, flat emitter. In this way, the excitation light can already be distributed more equally before entering the mixing rod.

The first mixing rod end face, can directly, abut the second rod end face of the glass rod and/or the end faces at the second fiber ends of every optical fiber. By arranging the second rod end face and/or the end faces at the second fiber ends to abut the first mixing rod end face, a space-saving configuration of the illumination device can be achieved, that can prevent a loss of intensity. The first mixing rod end face can be flush with and contact the second rod end face and/or the end faces at the second fiber ends of every optical fiber. According to an embodiment, the first mixing rod end face can directly abut the end faces at the second fiber ends of every optical fiber. This can enhance the coupling or injection of the excitation light into the mixing rod. The first mixing rod end face can be glued to the second rod end face of the glass rod and/or the end faces at the second fiber ends of every optical fiber with an optical glue. The optical glue, also known as optical cement or optical putty, can hold the glass rod, the optical fibers and the mixture rod together and reduces losses of light intensity at the interface.

According to a first embodiment, the second fiber ends are glued to the circumferential surface of the glass rod. The second fiber ends can be glued to the circumferential surface of the glass rod to form the annular, flat emitter. The end faces of the second fiber ends can be polished after gluing the second fiber ends to the circumferential surface of the glass rod. According to a second embodiment, the second fiber ends can be melted together to form a ring shape before being arranged on the circumferential surface of the glass rod. In other words, the second fiber ends can be first melted together to form the ring shape. Afterwards, the ring shape can be arranged on the circumferential surface of the glass rod. In the second embodiment, the second fiber ends can be polished before or after melting them together to form the ring shape. While the first embodiment does not require the ring to be shaped in advance, the second embodiment provides for an easier assembly once the second fiber ends are melted together.

An area of the first mixing rod end face of the mixing rod can be at least as large as an area of the second rod end face of the glass rod plus an annular fiber end face area, wherein the annular fiber end face area surrounds the second rod end face and comprises the end faces of the second fiber ends of all optical fibers. By configuring the first mixing rod end face this large, the mixing rod can receive the intensity of the white light and the excitation light without significant losses. The annular fiber end face area can be the annular, flat emitter. It is, in other words, the area that emits the excitation light. The annular fiber end face area can comprise the end faces of the second fiber ends of all optical fibers and the space in between.

The glass rod, the mixing rod and the second fiber ends can be surrounded by an outer sleeve. The outer sleeve holds the components of the illumination device together and can also dissipate heat generated in the illumination device. According to an embodiment, the outer sleeve can directly surround the circumferential surface of the mixture rod and a section of the optical fibers running along the circumferential surface of the glass rod. According to an alternative embodiment, an inner sleeve can directly surround the section of the optical fibers running along the circumferential surface of the glass rod. In this way, the inner sleeve can envelop both the optical fibers and the glass rod. In the alternative embodiment, the outer sleeve can directly surround the inner sleeve and the circumferential surface of the mixture rod. The outer and/or the inner sleeve can be a metal sleeve. Metal can provide a high stability and good heat conduction.

The plurality of optical fibers can be bundled into a plurality of fiber groups, each fiber group comprising multiple optical fibers, wherein the first fiber ends of the optical fibers of each fiber group can be melted together to form a combined first fiber end for each fiber group. The combined first fiber ends of the fiber groups can be utilized to couple the excitation light into the optical fibers. The first fiber ends can be glued together instead of being melted together. However, when exposed to a high energy density of a focused laser, the glue may melt. The melting of the multiple optical fibers together instead of gluing them together results in the combined first fiber end being much more resistant to high temperatures resulting from high energy densities. The intensity of the incoming excitation light can be distributed among the optical fibers, thus preventing damage to the first fiber ends when receiving excitation light from high powered excitation sources. Each fiber group can comprise at least ten, such as, at least a hundred optical fibers. For example, each fiber group can comprise a hundred to two hundred optical fibers.

The excitation light guide portion can comprise a plurality of excitation light sources arranged to couple the excitation light into the first fiber ends of the optical fibers, wherein the plurality of excitation light sources can comprise laser sources, such as laser diodes, wherein the plurality of excitation light sources can comprise light sources with at least two, or at least three, distinct, different wavelengths. By providing a plurality of excitation light sources, the excitation light can be coupled efficiently and homogeneously into the optical fibers. Laser sources, such as laser diodes as excitation sources for fluorescence image guided surgery can provide distinct wavelengths and high intensity required for this method. By providing at least two or three distinct, different wavelengths of excitation light, different fluorescent dyes can be utilized during the same surgery, improving the clarity and contrast of the image. In addition, the same illumination device can be utilized for different fluorescent dyes without changing the excitation sources. The plurality of excitation light sources can be arranged in front of the first fiber ends. A lens can be arranged in between each of the plurality of excitation light sources and the respective first fiber ends. In this way, the excitation light can be focused on and coupled into the first fiber ends.

Every light source of the plurality of excitation light sources can be aris ranged to couple the excitation light into a different combined first fiber end, wherein the plurality of excitation light sources can comprise at least two excitation light sources with identical wavelength arranged to couple the excitation light into different combined first fiber ends. Accordingly, a single excitation light source can be provided for every combined first fiber end. This can allow for an efficient transmission of the excitation light into the optical fibers. By providing at least two light sources with identical wavelength, the intensity of this particular wavelength can be easily increased without needing to adjust the intensity of individual light sources.

The white light guiding portion can comprise at least one white light source, the at least one white light source can be arranged to couple the white light into the first rod end of the glass rod, wherein the at least one white light source can comprise a white light LED and/or a white light source based on laser-excited phosphor, such as a plurality of white light LEDs and/or white light sources based on laser-excited phosphor. White light LEDs can provide the necessary intensity and have a high durability. A white light source based on laser-excited phosphor, sometimes known as white light laser, can also provide a high intensity. The at least one white light source can be arranged in front of the first rod end.

The white light guiding portion can comprise at least one total internal reflection lens arranged to receive the white light and to couple the white light into the first rod end of the glass rod, wherein the at least one total internal reflection lens can be arranged in between the at least one white light source and the first rod end of the glass rod. A total internal reflection lens, also known as TIR lens, can provide a very high coupling efficiency. Usually, this high intensity can be problematic when coupling the white light from the TIR lens directly into an optical fiber. However, as the white light can instead be coupled into the glass rod, there is no need to limit the white light intensity.

Such object can be further solved by a surgical instrument for fluorescence image guided surgery comprising an illumination device according to any of the previously discussed embodiments, wherein the surgical instrument can be an endoscope.

The same or similar advantages apply to the surgical instrument as were previously mentioned with respect to the illumination device.

The illumination device can be especially useful for an endoscope or other surgical instruments for minimal invasive surgery, as it provides homogenized mixed light of high intensity.

BRIEF DESCRIPTION OF THE DRAWINGS

Further characteristics will become apparent from the description of the embodiments together with the claims and the included drawings. Embodiments can fulfill individual characteristics or a combination of several characteristics.

The embodiments are described below, without restricting the general intent of the invention, based on exemplary embodiments, wherein reference is made expressly to the drawings with regard to the disclosure of all details that are not explained in greater detail in the text. In the drawings.

In the drawings, the same or similar types of elements or respectively corresponding parts are provided with the same reference numbers in order to prevent the item from needing to be reintroduced.

DETAILED DESCRIPTION

Figure 1:
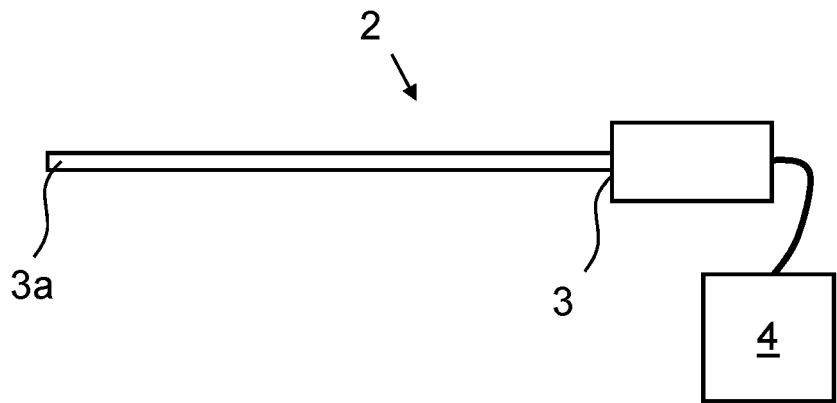
FIG. 1 illustrates a schematic simplified representation of a surgical instrument with an illumination device.

FIG. 1 shows a schematic simplified representation of a surgical instrument 2, for example an endoscope. The surgical instrument 2 comprises a body 3 with a distal end 3a, which is configured to enter a cavity of a patient. An illumination device 4 is provided, which is connected to the body 3 to provide illumination during a surgery, for example in the form of white light 11.

In fluorescence image guided surgery, certain regions in the surgical area are marked with special fluorescent dyes, which emit fluorescent light when exposed to excitation light of a particular wavelength. In this way, the marked regions are highlighted to assist the surgeon during the surgery. However, to stimulate the fluorescent dyes, excitation light 21 has to be directed to the surgical area in addition to the white light 11.

Figure 2:
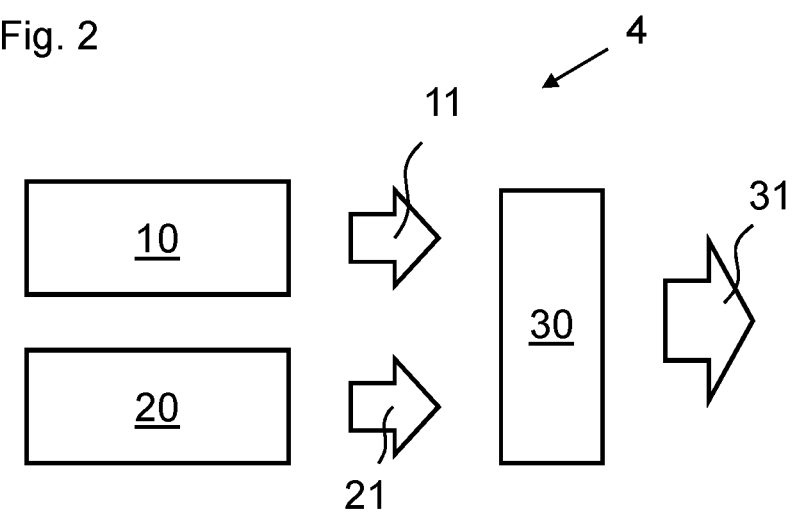
FIG. 2 illustrates a schematic simplified representation of an illumination device with a white light guiding portion, an excitation light guiding portion and a mixed light guiding portion.

FIG. 2 shows a schematic simplified representation of an illumination device 4 able to emit both white light 11 and excitation light 21. The illumination device 4 comprises a white light guiding portion 10, an excitation light guiding portion 20 and a mixed light guiding portion 30. The white light guiding portion 10 and the excitation light guiding portion 20 guide the white light 11 and the excitation light 21, respectively, and couple it into the mixed light guiding portion 30. In the mixed light guiding portion 30, both the white light 11 and the excitation light 21 are guided until they are emitted as mixed light 31.

For example, the white light guiding portion 10 and the excitation light guiding portion 20 may both be optical fibers and the mixed light guiding portion 30 may be an optical fiber cable, which is flush with or in proximity to the optical fibers of the white light guiding portion 10 and the excitation light guiding portion 20. However, configuring all the guiding portions 10, 20, 30 as optical fibers has disadvantages. For example, the optical fibers in the guiding portions 10, 20 may be damaged when exposed to high light intensities. There also may be a loss of intensity at the interface between the white light guiding portion 10 and the excitation light guiding portion 20 on the one hand and the mixed light guiding portion 30 on the other hand. Finally, the intensity of the white light 11 and the excitation light 21 may not be distributed equally in the mixed light guiding portion 30, leading to unnecessary bright spots in the mixed light 31.

Figure 3:
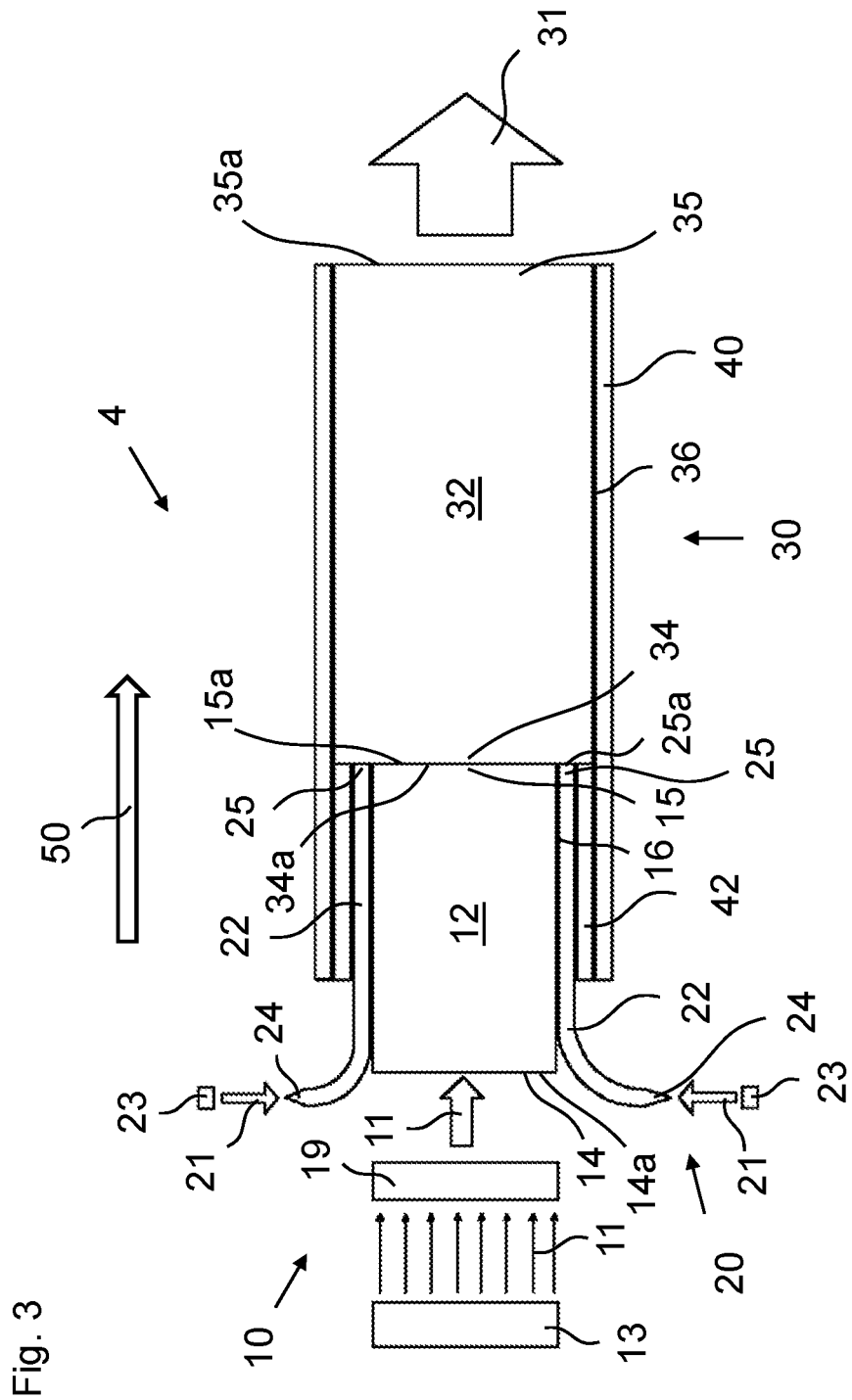
FIG. 3 illustrates a schematic simplified cross sectional representation of an illumination device.

FIG. 3 shows a schematic simplified cross section of an illumination device 4 that solves these issues. The white light guiding portion 10 of the illumination device 4 comprises a cylindrical glass rod 12 instead of an optical fiber. The glass rod 12 extends from a first rod end 14 to a second rod end 15 in a longitudinal direction 50. At the first rod end 14 the glass rod 12 comprises a first rod end face 14a and at the second rod end 15 a second rod end face 15a. Between the end faces 14a, 15a extends a circumferential surface 16. Such a glass rod 12 is better suited to receive high intensities of white light 11 and also homogenizes the white light 11 guided within. The white light guiding portion 10 further comprises a white light source 13, for example one or more white LEDs, and one or more total internal reflection lenses 19. Usually, one total internal reflection lens 19 is provided for every LED. The white light 11 emitted by the white light source 13 is aligned by the total internal reflection lens 19 and afterwards coupled into the first rod face 14a of the glass rod 12.

The excitation light guiding portion 20 comprises a plurality of optical fibers 22, which each extend from a first fiber end 24 to a second fiber end 25. The first fiber ends 24 are arranged to receive the excitation light 21 from excitation light sources 23, for example laser sources. The second fiber ends 24 are arranged surrounding the circumferential surface 16 of the glass rod 12, so that the second fiber ends 25 emit the excitation light 21 essentially in the longitudinal direction 50. According to one embodiment, the second fiber ends 25 are glued to the circumferential surface 16 in a ring like fashion. In another embodiment, the second fiber ends 25 are melted together to form a ring shape, which is placed on top of the circumferential surface 16. In any case, the resulting arrangement leads to an annular fiber end face area, which emits the excitation light 21 in a ring-like fashion. This ring-like excitation light 21 surrounds the white light 11 emitted by the glass rod 12.

The mixed light guiding portion 30 comprises a mixing rod 32, which extends from a first mixing rod end 34 with a first mixing rod end face 34a to a second mixing rod end 35 with a second mixing rod end face 35a, spanning a circumferential surface 36 in between them. The first mixing rod end face 34a abuts both the second rod end face 15a of the glass rod 12 and end faces 25a of the second fiber ends 25 of the optical fibers 22. Thus, the white light 11 and the excitation light 21 are coupled into the mixing rod 32, where they are mixed and homogenized. The homogenized mixed light 31 comprising both the white light 11 and the excitation light 21 is emitted from the second mixing rod end face 35a. This mixed light 31 does not comprise any bright light spots of the excitation light 21 or the white light 11, as the intensity of the mixed light 31 is distributed equally around the second mixing rod end face 35a.

The mixing rod 32 may be made from glass or transparent plastic, while the glass rod 12 is made from glass to better withstand high intensities of white light 11. The glass rod 12 and the second fiber ends 25 of the optical fibers 22 are at least partially surrounded by an inner sleeve 42, which is for example made of metal. This inner sleeve 42 holds the optical fibers 22 and the glass rod 12 together and dissipates heat. Also, the inner sleeve 42 allows the end faces 25a of the optical fibers 22 to be easily polished, before the mixing rod 32 is placed in front of the end faces 25a. An outer sleeve 40 is placed surrounding the inner sleeve 42 and a circumferential surface 36 of the mixing rod 32. Just like the inner sleeve 42, the outer sleeve 40 holds the components together and dissipates heat.

Figure 4:
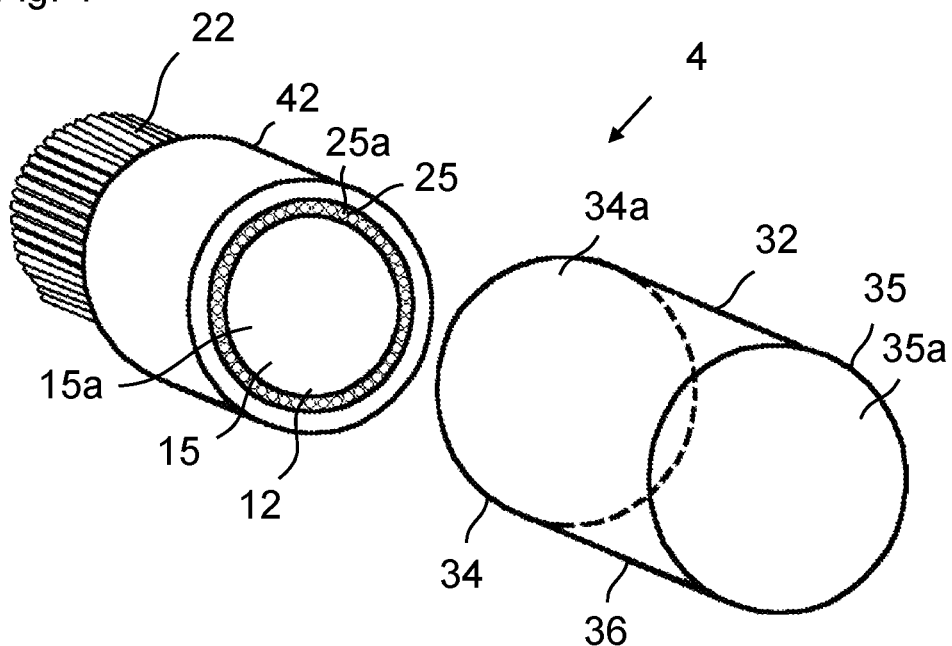
FIG. 4 illustrates a schematic simplified perspective representation of an illumination device.

FIG. 4 shows a schematic simplified perspective representation of the illumination device 4 without the outer sleeve 40. In addition, the mixing rod 32 is shown removed from the other components to better visualize their internal structure. In FIG. 4, the ring-like arrangement of the optical fibers 22 is visible. To increase clarity, only one of the optical fibers 22 is provided with reference sign and the first fiber ends 24 are omitted. In addition, the number of optical fibers 22 is reduced, as there are usually hundreds or thousands of optical fibers 22 arranged around the glass rod 12. In any case, FIG. 4 shows that the end faces 25a of the second fiber ends 25 form an annular, flat emitter surrounding the second rod end face of the glass rod 12. The first mixing rod end face 34a in this example is at least as big as a combined area of the end face 15a of the glass rod 12, the end faces 25a of the optical fibers 22 and the end face of the inner sleeve 42.

Figure 5:
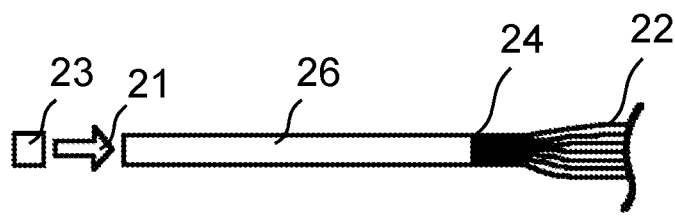
FIG. 5 illustrates a schematic simplified representation of a combined first fiber end and an excitation light source and FIG. 6 illustrates a schematic simplified representation of a glass rod and a mixture rod with a rod core and cladding.

FIG. 5 shows a schematic simplified representation of multiple first fiber ends 24 of optical fibers 22 of a fiber group, which are melted together to form a combined first fiber end 26. Once again, only one of the optical fibers 22 is provided with reference sign. While in FIG. 5 only seven optical fibers 22 are melted together, in reality hundreds of optical fibers 22 may be melted together to form the combined first fiber end 26. The combined first fiber end 26 is better suited to receive high intensity excitation light 21 from excitation light sources 23 with high intensity output, for example laser diodes and/or LEDs. Coupling this high intensity into a single first fiber end 24 would damage the first fiber end 24 due to the resulting heat. However, by combining the first fiber ends 24 to a combined first fiber end 26, the intensity equally distributed among the optical fibers 22, thus preventing damage.

Figure 6:
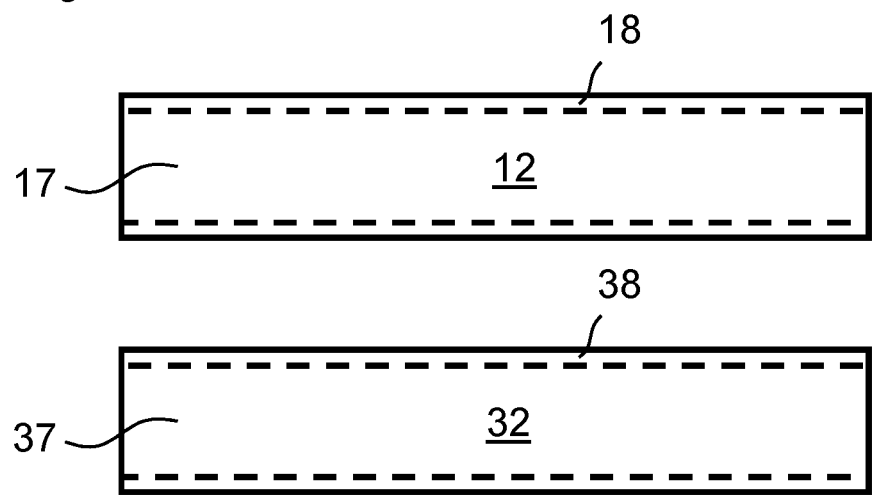

FIG. 6 shows a schematic simplified representation of a glass rod 12 with a rod core 17 and a cladding 18 as well as a mixture rod 32 with a rod core 37 and a cladding 38. The claddings 18, 38 surround the circumference of the respective rod core 17, 37 and have a lower refractive index than the rod cores 17, 37. In this way, the claddings 18, 38 prevent light 11, 21 guided in the rod core 17, 37 to leave the rod 12, 32 through the circumferential surface 16, 36. In addition, the length of the rods 12, 32 is more than five times greater than their diameter, which results in increased homogenization of the guided light.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES 2 surgical instrument
3 body
3a distal end
4 illumination device
10 white light guiding portion
11 white light
12 glass rod
13 white light source
14 first rod end
14a first rod end face
15 second rod end
15a second rod end face
16 circumferential surface
17 rod core
18 cladding
19 total internal reflection lens
20 excitation light guiding portion
21 excitation light
22 optical fiber
23 excitation light source
24 first fiber end
25 second fiber end
25a end face
26 combined first fiber end
30 mixed light guiding portion
31 mixed light
32 mixing rod
34 first mixing rod end
34a first mixing rod end face
35 second mixing rod end
35a second mixing rod end face
36 circumferential surface
37 rod core
38 cladding
40 outer sleeve
42 inner sleeve
50 longitudinal direction

What is claimed is:

1. An illumination device for use in fluorescence image guided surgery, the illumination device comprising:
a white light guiding portion;
an excitation light guiding portion; and
a mixed light guiding portion;
wherein the white light guiding portion comprises a glass rod extending in a longitudinal direction from a first rod end configured to receive white light, to a second rod end configured to emit the white light, the glass rod comprising a first rod end face at the first rod end, a second rod end face at the second rod end and a circumferential surface extending between the first rod end face and the second rod end face;
the excitation light guiding portion comprises a plurality of optical fibers, each extending from a first fiber end configured to receive excitation light, to a second fiber end configured to emit the excitation light, the second fiber ends of the plurality of optical fibers being configured to surround the circumferential surface of the glass rod at the second rod end;
the mixed light guiding portion comprises an optical mixing rod extending in the longitudinal direction from a first mixing rod end configured to receive the white light and the excitation light, to a second mixing rod end configured to emit mixed light, the mixing rod comprising a first mixing rod end face at the first mixing rod end, a second mixing rod end face at the second mixing rod end and a circumferential surface extending between the first mixing rod end face and the second mixing rod end face;
the glass rod is arranged to couple the white light guided in the glass rod into the mixing rod via the second rod end face of the glass rod and the first mixing rod end face of the mixing rod; and
each of the plurality of optical fibers are arranged to couple the excitation light guided in the plurality of optical fibers into the mixing rod via end faces at the second fiber ends of the plurality of optical fibers and the first mixing rod end face of the mixing rod.

2. The illumination device according to claim 1, wherein one or more of the glass rod and the mixture rod has a cylindrical shape.

3. The illumination device according to claim 2, wherein the second fiber ends of the plurality of optical fibers are arranged to completely surround the circumferential surface at the second rod end of the glass rod.

4. The illumination device according to claim 1, wherein one or more of the glass rod and the mixture rod comprises a rod core and a cladding, wherein the cladding surrounds the rod core along a circumference of the rod core and has a lower refractive index than the rod core.

5. The illumination device according to claim 2, wherein a length of the mixture rod is at least five times greater than a diameter of the mixture rod.

6. The illumination device according to claim 1, wherein the second fiber ends are arranged to form an annular, flat emitter around a periphery of the second rod end of the glass rod.

7. The illumination device according to claim 1, wherein the first mixing rod end face abuts one or more of the second rod end face of the glass rod and the end faces at the second fiber ends of each of the plurality of optical fibers.

8. The illumination device according to claim 7, wherein the first mixing rod end face directly abuts one or more of the second rod end face of the glass rod and the end faces at the second fiber ends of each of the plurality of optical fibers.

9. The illumination device according to claim 1, further comprising an adhesive for gluing the second fiber ends to the circumferential surface of the glass rod.

10. The illumination device according to claim 1, wherein the second fiber ends being melted together to form a ring shape before being arranged on the circumferential surface of the glass rod.

11. The illumination device according to claim 1, wherein an area of the first mixing rod end face of the mixing rod is at least as large as an area of the second rod end face of the glass rod plus an annular fiber end face area, wherein the annular fiber end face area surrounds the second rod end face and comprises the end faces of the second fiber ends of the plurality of optical fibers.

12. The illumination device according to claim 1, further comprising an outer sleeve surrounding the glass rod, the mixing rod and the second fiber ends.

13. The illumination device according to claim 1, wherein the plurality of optical fibers are bundled into a plurality of fiber groups, each fiber group comprising multiple optical fibers of the plurality of optical fibers, wherein the first fiber ends of the multiple optical fibers of each fiber group being melted together to form a combined first fiber end for each fiber group.

14. The illumination device according to claim 1, wherein the excitation light guide portion comprises a plurality of excitation light sources arranged to couple the excitation light into the first fiber ends of the plurality of optical fibers.

15. The illumination device according to claim 14, wherein the plurality of excitation light sources comprise laser sources.

16. The illumination device according to claim 15, wherein the plurality of excitation light sources comprises light sources with at least two different wavelengths.

17. The illumination device according to claim 1, wherein:
the excitation light guide portion comprises a plurality of excitation light sources arranged to couple the excitation light into the first fiber ends of the plurality of optical fibers; and
each light source of the plurality of excitation light sources is arranged to couple the excitation light into a different combined first fiber end of the plurality of fiber groups.

18. The illumination device according to claim 17, wherein the plurality of excitation light sources comprises at least two excitation light sources with identical wavelength arranged to couple the excitation light into corresponding combined first fiber ends.

19. The illumination device according to claim 1, wherein the white light guiding portion comprises at least one white light source, the at least one white light source being arranged to couple the white light into the first rod end of the glass rod.

20. The illumination device according to claim 19, wherein the at least one white light source comprises a white light LED or a white light source based on laser-excited phosphor.

21. The illumination device according to claim 1, wherein the white light guiding portion comprises at least one total internal reflection lens arranged to receive the white light and to couple the white light into the first rod end of the glass rod.

22. The illumination device according to claim 21, wherein the at least one total internal reflection lens is arranged in between at least one white light source and the first rod end of the glass rod.

23. A surgical instrument for use in fluorescence image guided surgery, the surgical instrument comprising the illumination device according to claim 1.

* * * * *